United States Patent [19]

Fenical et al.

[11] Patent Number: 6,066,635
[45] Date of Patent: May 23, 2000

[54] AVRAINVILLAMIDE, A CYTOTOXIC MARINE NATURAL PRODUCT, AND DERIVATIVES THEREOF

[75] Inventors: William Fenical, Del Mar; Paul R. Jensen, San Diego; Xing C. Cheng, Long Beach, all of Calif.

[73] Assignee: University of California, San Diego, San Diego, Calif.

[21] Appl. No.: 09/274,899

[22] Filed: Mar. 23, 1999

[51] Int. Cl.[7] ............... A61K 31/4985; A61K 31/4995; C07D 241/00
[52] U.S. Cl. ............ 514/250; 514/247; 514/248; 514/249; 544/339; 544/358
[58] Field of Search ................... 544/339, 358; 514/250, 249, 248, 247

[56] References Cited

U.S. PATENT DOCUMENTS 5,473,057  12/1995  Fenical et al. ..................... 536/17.3

OTHER PUBLICATIONS

Fenical et al., J. Amer. Chem. Soc., 113 (6) 2303–4 (A65), 1991.
Atherton and Shephard, *Solid Phase Peptide Synthesis—A Practical Approach*, IRL Press, Oxford England, (1989).
Bodanzsky, *Principles of Peptide Synthesis*, 1st Revised Edition, Springer–Verlag, N.Y., (1984).
Bodanzsky, *Principles of Peptide Synthesis*, 2nd Revised Edition, Springer–Verlag, N.Y., (1984).
Greene and Wuts, *Protective Groups in Organic Synthesis*, Second edition, John Wiley and Sons, New York, Chapters 2, 3, and 7, (1991).
Reese and Haslam, *Protective Groups in Organic Chemistry*, McOmie, Plenum Press, New York NY, Chapters 3 and 4, (1973).
Stewart and Young, *Solid Phase Peptide Synthesis*, 2nd Edition, W.H. Freeman & Company, San Francisco (1984).

*Primary Examiner*—Mukund J. Shah
*Assistant Examiner*—Pavanaram K Sripada
*Attorney, Agent, or Firm*—Campbell & Flores LLP

[57] ABSTRACT

The present invention provides a compound having the structure

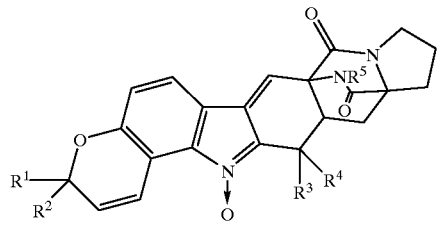

wherein,
$R^1$, $R^2$, $R^3$, $R^4$ and $R^5$ are independently selected from H, alkyl, aminoalkyl, perfluoroalkyl, or pharmaceutically acceptable salts thereof, useful for treating cancer.

13 Claims, No Drawings

AVRAINVILLAMIDE, A CYTOTOXIC MARINE NATURAL PRODUCT, AND DERIVATIVES THEREOF

This invention was made with government support under grants CA 44848 and CA 67775 awarded by the National Cancer Institute. The government has certain rights in the invention.

BACKGROUND OF THE INVENTION

1. Field of the Invention

This invention relates generally to the fields of biochemistry and medicine, and more specifically to compounds useful as cancer chemotherapeutic agents.

2. Background Information

Cancer is a leading cause of death in the United States. Despite significant efforts to find new approaches for treating cancer, surgery, chemotherapy and radiation therapy, either alone or in combination, remain the methods of choice. Surgery and radiation therapy, however, generally are useful only for fairly defined cancers and are of limited use for treating patients with disseminated disease.

Chemotherapy is the method of choice for treating patients with metastatic cancer or patients with diffuse cancers such as leukemia. Although chemotherapy can provide a therapeutic benefit in many cancer patients, it often fails to result in cure of the disease due to the patient's cancer cells becoming resistant to the chemotherapeutic agent. Due, in part, to the likelihood of cancer cells becoming resistant to a chemotherapeutic agent, these drugs commonly are used in combination to treat patients.

A continuing effort is being made by individual academic investigators, and by large and small pharmaceutical companies to identify new and useful chemotherapeutic agents. Various drug/agent strategies have been developed. In some instances, derivatives of known effective drugs are prepared and examined for improved or different, but useful characteristics. Another approach is to develop or acquire large libraries of randomly synthesized drugs candidates, and screen these compounds for potential efficacy as chemotherapeutic agents. Both of these methods have resulted in the identification of potentially useful agents. Yet another approach has been to identify potentially useful drugs that are produced naturally by living organisms. For example, paclitaxel is a compound that is produced by the yew tree and, when purified, is effective in treating cancers such as ovarian carcinoma.

Despite the identification of such new chemotherapeutic agents, there is still an unmet need for additional compounds that can be used to treat diseases such as cancer. The present invention addresses this need, as well as provides for additional advantages.

SUMMARY OF THE INVENTION

The present invention provides a compound having the structure

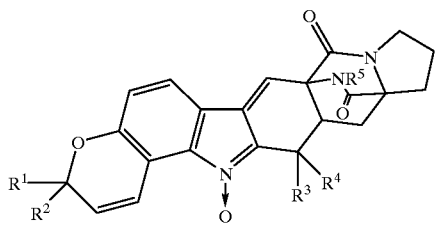

wherein,
R$^1$, R$^2$, R$^3$, R$^4$ and R$^5$ are independently selected from H, alkyl, aminoalkyl, perfluoroalkyl;
or pharmaceutically acceptable salts, useful for treating cancer.

DETAILED DESCRIPTION OF THE INVENTION

The present invention provides a compound having the structure,

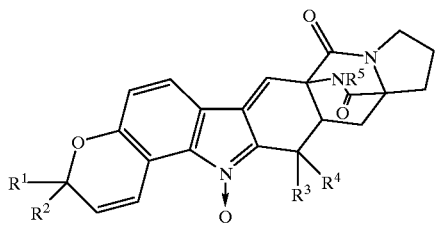

wherein,
R$^1$, R$^2$, R$^3$, R$^4$ and R$^5$ are independently selected from H, alkyl, aminoalkyl or perfluoroalkyl,
or pharmaceutically acceptable salts.

For example, the invention provides Avrainvillamide (CNC 358.445) having the chemical structure:

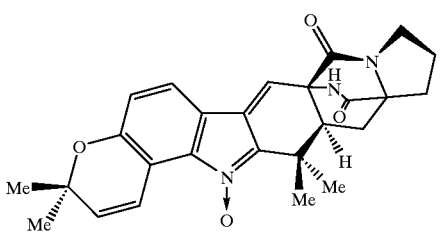

The invention also provides pharmaceutical compositions comprising a compound of the invention, or a pharmaceutically acceptable salt thereof, and a pharmacologically acceptable carrier.

The invention further provides a method of reducing or inhibiting the viability of a cell by contacting the cell with a compound of the invention. As such, the invention provides a method of reducing the severity of a pathology characterized, at least in part, by undesirable proliferation of a population of cells in a subject by administering to the subject a compound of the invention in an amount sufficient to reduce or inhibit proliferation of the population of cells. For example, the invention provides a method of treating a cancer patient by administering to the patient a compound of the invention in an amount sufficient to reduce or inhibit proliferation of cancer cells in the patient.

Avrainvillamide is isolated from the fermentation of a marine fungus, Aspergillus sp. CNC358, which was collected in the waters off the Bahamas Islands and has been deposited with the American Type Culture Collection as Accession No. ATCC 74476 (Rockville Md.).

Definitions:

As used herein, the term "alkyl" means a carbon moiety of one to twelve carbon atoms, such as methyl, ethyl, propyl, butyl, pentyl, hexyl, heptyl, octyl, nonyl, decyl, undecyl, and dodecyl. The carbon moieties may be linear (for example, n-butyl, n-propyl, n-pentyl and such) or branched (for example i-propyl, t-butyl, 2-methylpentyl, 2-ethylhexyl, and such).

As used herein, the term "aminoalkyl" means an alkyl moiety or radical substituted with an amino functionality, the substitution maybe at a primary, secondary or tertiary position on the alkyl moiety resulting in the respective, primary, secondary or tertiary substituted aminoalkyl moiety or radical. For example, 1-aminomethyl, 1-aminoethyl, 1-amino-2-methylethyl, 1-aminopropyl, 2-aminopropyl, 1-aminobutyl, 2-aminobutyl, 3-aminobutyl, 1-aminopentyl and such. Aminoalkyl moieties can be used to derivatize compounds of the current invention to change the physical characteristics of a compound, such as its solubility, or the enable the compound to form a salt, or more preferably a pharmaceutically acceptable salt, without impairing the activity of the compound.

As used herein, the term "perfluoroalkyl" means an alkyl moiety or radical where all the hydrogen atoms have been replaced by fluorine atoms. For example, perfluoromethyl refers to $CF_3$—, perfluoroethyl refers to $CF_3CF_2$—, and perfluoropropyl refers to $CF_3CF_2CF_2$—.

As used herein, the term "pharmaceutically acceptable salt" or "salt" encompasses those salts that form with the carboxylate anions and includes salts formed with the organic and inorganic cations such as those chosen from the alkali and alkaline earth metals, (for example, lithium, sodium, potassium, magnesium, barium and calcium); ammonium ion; and the organic cations (for example, dibenzylammonium, benzylammonium, 2-hydroxyethylammonium, phenylethylbenzylammonium, bis(2-hydroxyethyl)ammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Further included are salts that form by standard acid-base reactions with basic groups (such as amino groups), including organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic acids, and the like.

The compounds of the above structure may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

As used herein, the term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, benzyl, allyl, 4,4',4"-trimethoxytrityl, trimethylsilyl, (t-butyl) dimethylsilyl, 2,2,2-trichloroethoxycarbonyl, and the like. Further examples of hydroxy-protecting groups are described by Reese and Haslam, "Protective Groups in Organic Chemistry" (McOmie, Ed., Plenum Press, New York, N.Y., 1973), Chaps. 3 and 4; and Greene and Wuts, "Protective Groups in Organic Synthesis," Second Edition (John Wiley and Sons, New York, 1991), Chaps. 2 and 3; each of which is incorporated herein by reference. A preferred hydroxy-protecting group is the tert-butyl group. The related term "protected hydroxy" denotes a hydroxy group bonded to one of the above hydroxy-protecting groups.

As used herein, the term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("Boc"), 2-(4-biphenylyl) propyl-2-oxycarbonyl, 2-phenylpropyl-2-oxycarbonyl, 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl, 2-(p-toluyl) propyl-2-oxycarbonyl, cyclopentanyloxycarbonyl, 1-methylcyclopentanyl-oxycarbonyl, cyclohexanyloxycarbonyl, 1-methyl-cyclohexanyloxycarbonyl, 2-methylcyclohexanyl-oxycarbonyl, 2-(4-toluylsulfonyl) ethoxycarbonyl, 2-(methylsulfonyl)ethoxycarbonyl, 2-(triphenylphosphino)-ethoxycarbonyl, 9-fluorenylmethoxycarbonly ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, 4-methoxybenzyloxycarbonyl, α-2,4,5,-tetramethylbenzyl-oxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl and the like; the benzoylmethylsulfonyl group, the 2,2,5,7,8-pentamethylchroman-6-sulfonyl group, the dithiasuccinoyl group, the 2-(nitro)phenyl-sulfenyl group, the diphenylphosphine oxide group, and like amino-protecting groups.

The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described, for example, by Greene and Wuts, supra, 1991, Chap. 7; Bodanzsky, "Principles of Peptide Synthesis," 1st and 2nd revised Ed. (Springer-Verlag, New York, 1984 and 1993); Stewart and Young, "Solid Phase Peptide Synthesis," 2nd Ed. (Pierce Chemical Co., Rockford Ill., 1984); Atherton and Shephard, "Solid Phase Peptide Synthesis—A Practical Approach" (IRL Press, Oxford England, 1989), each of which is incorporated herein by reference. The related term "protected amino" defines an amino group substituted with an amino-protecting group discussed above.

Depending on the choice of solvent and other conditions known to the practitioner skilled in the art, compounds of this invention may also take the ketal or acetal form, which forms are included in the instant invention. In addition, it should be understood that the equilibrium forms of the compounds of this invention may include tautomeric forms. All such forms of these compounds are expressly included in the present invention.

The compounds of the invention can be modified by appropriate functionalities to enhance selective biological properties. Such modifications are known in the art and include those which increase biological penetration into a given biological system, for example, blood, the lymphatic system, or the central nervous system, increase oral availability, increase solubility to allow administration by injection, alter metabolism and alter rate of exertion. In addition, the compounds can be altered to a pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups.

As used herein, the term "N→O" refers to a N-oxide moiety.

As used herein, the term "reducing or inhibiting" means that a parameter is decreased due to an action of a compound of the invention as compared to the parameter in the absence of any action by a compound of the invention. For example, the term "reducing or inhibiting," when used in reference to cell viability or to cell proliferation, means that survival or proliferative activity of cells contacted with a compound of the invention is less than the survival or proliferation in the absence of the compound. The terms "reduce" and "inhibit" are used together herein because it is recognized that, depending on the particular assay used to examine a parameter, the limit of detection of the assay may be such that it will not be able to be determined whether the parameter is inhibited or is reduced below the level of detection of the assay. For example, the ability of the cells to proceed through mitosis in the presence of a compound of the invention may be completely inhibited, i.e., 100% of the cells are blocked in a premitotic stage, or may be reduced such that 90% or 99% of the cells are blocked in a premitotic stage. It should be recognized, however, that regardless of whether the recited parameter is "reduced" or is "inhibited," the level of the parameter as determined in the presence of a compound of the invention will be measurably decreased as compared to the level the parameter would be in the absence of the compound.

The Invention:

The compounds of the invention can be isolated in substantially purified form from Aspergillus sp. CNC358, then can be chemically modified as desired to contain one or more of the substituents discussed above. As used herein, the term "isolated" or "substantially purified" means that the compound of the invention is at least about 50% free of materials with which it normally is associated in a cell, and generally is about 90% or 95% free of such materials, particularly at least 99% free of such material.

If desired, a compound of the invention can be in the form of a pharmaceutical composition, comprising the compound or a salt thereof, and a pharmaceutically acceptable carrier. Pharmaceutically acceptable carriers, which can be an adjuvant or other vehicle, include, but are not limited to, ion exchange resins, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat, and the like.

As disclosed herein, Avrainvillamide produced a dose dependent cytotoxic effect against a variety of tumor cell lines in the NCI 60 cell panel, including human colon HCT116 cells ($IC_{50}$=2.0 µg/ml), melanoma MALME-3M cells ($IC_{50}$=53 nM) and two breast cancer cells, βT-549 ($IC_{50}$=34 nM) and T-47D ($IC_{50}$=72 nM), wherein the term "$IC_{50}$" means the drug concentration required to inhibit cell proliferation by 50% as compared to untreated cells. Thus, the invention provides a method of treating a cancer patient by administering to the patient a compound of the invention in an amount sufficient to reduce or inhibit proliferation of cancer cells in the patient.

Administration

A compound of the invention, when administered to a subject such as a mammalian subject, for example, a human, can be administered orally, parenterally, by inhalation, topically, rectally, nasally, buccally or vaginally, and can be contained in an implanted reservoir. Parenteral administration can be by subcutaneous, intracutaneous, intravenous, intramuscular, intra-articular, intrasynovial, intrasternal, intrathecal, intralesional or intracranial injection or by an infusion method.

A compound of the invention, which can comprise a pharmaceutical composition, can be in the form of a sterile injectable preparation, for example, a sterile injectable aqueous or oleaginous suspension. Such a suspension can be formulated by methods known in the art using, for example, suitable dispersing or wetting agents such as Tween 80, or suspending agents. The sterile injectable preparation also can be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic saline solution. In addition, sterile, fixed oils are conventionally employed as a solvent or suspending medium. For this purpose, any bland fixed oil can be employed, including synthetic monoglycerides or diglycerides. Fatty acids such as oleic acid and its glyceride derivatives also are useful in the preparation of injectables, as are natural pharmaceutically acceptable oils such as olive oil or castor oil, especially in their polyoxyethylated versions. These oil solutions or suspensions also can contain a long chain alcohol diluent or dispersant.

A compound of the invention can be orally administered in any orally acceptable dosage form including, but not limited to, capsules, tablets and aqueous suspensions and solutions. In the case of tablets for oral use, carriers that commonly are used include lactose and corn starch. Lubricating agents such as magnesium stearate also can be added.

For oral administration in capsule form, useful diluents include lactose and dried corn starch. When aqueous suspensions are administered orally, the active ingredient can be combined with emulsifying and suspending agents. If desired, certain sweetening, flavoring or coloring agents can be added.

A compound of the invention also can be formulated in a pharmaceutical composition for administration in the form of suppositories for rectal administration. Such a composition can be prepared by mixing a compound of the invention, for example, Avrainvillamide, with a suitable non-irritating excipient that is solid at room temperature, but liquid at the rectal temperature. Such materials include, but are not limited to, cocoa butter, beeswax and polyethylene glycols. Topical administration of a compound of the invention can be particularly useful when the desired treatment involves areas or organs readily accessible to topical application. For application topically to the skin, for example, the compound should be formulated with a suitable ointment containing the active compound suspended or dissolved in a carrier, or can be in the form of a spray. Carriers for topical administration of the compounds of the invention include, but are not limited to, mineral oil, liquid petroleum, white petroleum, propylene glycol, polyoxyethylene, polyoxypropylene compound, emulsifying wax and water. A compound of the invention also can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. A compound also can be formulated to allow topically application to the lower intestinal tract by rectal suppository formulation or in a suitable enema formulation. Topically applied transdermal patches containing a compound of the invention are also included in this invention.

A compound of the invention also can be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, or other solubilizing or dispersing agents.

EXAMPLES

The following examples are given to enable those of ordinary skill in the art to more clearly understand and to practice the present invention. The examples should not be considered as limiting the scope of the invention, but merely as be illustrative and representative thereof.

Example 1

FERMENTATION AND ISOLATION OF AVRAINVILLAMIDE

The fermentation medium consisted of 0.5% yeast extract, 1% glucose, 100% seawater, 05% peptone, 0.2% crab meal. After 20 days static culture, the fungal mycelium was separated from 20 L broth and extracted in excess acetone, filtered, concentrated under vacuo and partitioned into EtOAc. The EtOAc extract was then subjected to silica chromatography, using a solvents mixture of isooctane and ethyl acetate, and then normal phase HPLC (100 % EtOAc) to yield Avrainvillamide possessing the following properties:

Avrainvillamide: Yellow gum, IR (film) 3424, 2966, 1689, 1365, 1021$cm^{-1}$, HRFABMS, MH+ m/z et. al., calcd. for $C_{26}H_{28}N_3O_4$: 446.2080, obsd 446.2088; $[\alpha]D=+10.6°$ (c=0.17, CHCl3), UV$\lambda$ max nm (MeOH) 370 ($\epsilon$ 2720), 280 ($\epsilon$ 6300).

The structures were assigned by spectroscopic methods including C-13 and proton nuclear magnetic resonance spectroscopy.

Example 2

PRODUCTION AND PURIFICATION OF AVRAINVILLAMIDE

The Avrainvillamide producing strain, tentatively identified as an Aspergillus sp., designated CNC358, was isolated from a sample of the green alga Avrainvillea sp. collected in the Bahamas. Aspergillus sp. CNC358 has been deposited with the American Type Culture Collection as Accession No. 74476.

The producing stain an Aspergillus sp., strain CNC358, was isolated from a sample of the green alga Avrainvillea sp. collected in the Bahamas. The sample was air dried then dissected into small pieces. The pieces were then placed onto a seawater based agar medium containing the antibiotics penicillin G and streptomycin sulfate to reduce bacterial growth. Following incubation, fungal hyphae were observed growing away from the alga and out onto the agar medium. A small piece of this growth was removed with a sterile scalpel and transferred to a fresh plate containing the agar medium. Following the development of adequate growth on this new plate, small pieces of the mycelium were cut away, placed in sterile vials containing the growth medium enriched with 10% glycerol, and cryopreserved at −80° C.

For Avrainvillamide production, CNC358 was cultured in 1 L of the marine-based medium YPG+C consisting of 1% glucose, 0.5% yeast extract, 0.5% peptone, 0.2% crab meal, 100% seawater. The fermentation culture was not shaken during the entire growth period of 21 days.

Following fermentation, the mycelium was filtered away from the broth and the cells freeze-dried and extracted twice with 500 ml acetone. The combined acetone ex tracts were filtered and concentrated by rotary evaporation. This crude extract was active in the HCT-116 cytotoxicity assay with an $IC_{50}$=7.8 $\mu$g/ml.

The active crude extract was partitioned into ethyl acetate (EtOAc) and the EtOAc subjected to silica chromatography using a solvent mixture of isooctane and EtOAc. The active fractions were subjected to normal phase HPLC (100% EtOAc) yielding a fine white powder that when acidified with 1N HCl was converted to a compound Avrainvillamide. The structure of the compound was elucidated by combined mass spectrometry, and proton and carbon NMR analysis.

Avrainvillamide is active against the human colon tumor cell line (HCT-116) with an $IC_{50}$=2.0 $\mu$g/ml. This compound showed significant selective in vitro cytotoxicity towards melanoma (MALME-3M) and breast cancers ($\beta$T-549 and T-470) at the National Cancer Institute with $IC_{50}$ values of 53 nM, 34 nM, and 72 nM, respectively.

We claim:
1. A compound of the structure

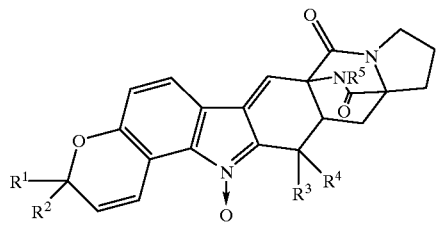

wherein,
$R_1$, $R^2$, $R^3$, $R^4$ and $R^5$ are independently selected from
H, alkyl, aminoalkyl, perfluoroalkyl,
or pharmaceutically acceptable salts thereof.

2. The compound of claim 1, wherein $R^1$, $R^2$, $R^3$ and $R^4$ are methyl.

3. The compound of claim 2, wherein $R^5$ is H.

4. A compound of the structure

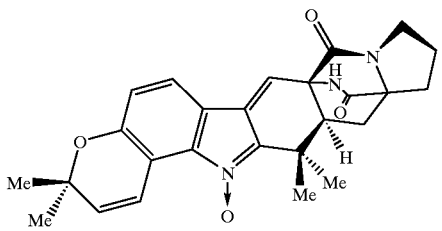

5. A pharmaceutical composition useful for treating cancer, comprising of a compound of the structure

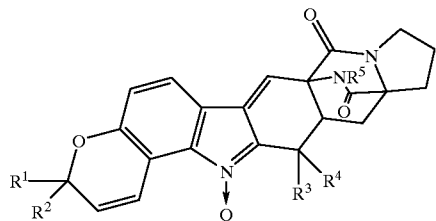

wherein,
$R^1$, $R^2$, $R^3$, $R^4$ and $R^5$ are independently selected from
H, alkyl, aminoalkyl, perfluoroalkyl, pharmaceutically acceptable salts thereof, and pharmaceutically acceptable excipients useful for treating cancer.

6. The compound of claim 5, wherein $R^1$, $R^2$, $R^3$ and $R^4$ are methyl.

7. The compound of claim 6, wherein $R_5$ is H.

8. A method of treating cancer with a compound of the structure

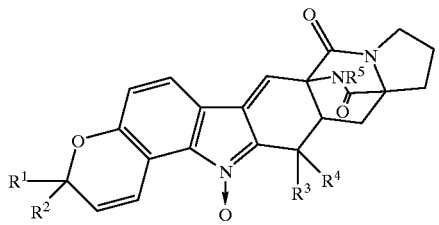

wherein,
$R_1$, $R^2$, $R^3$, $R^4$ and $R^5$ are independently selected from
H, alkyl, aminoalkyl, perfluoroalkyl, or
pharmaceutically acceptable salts thereof.

9. The method of claim 8, wherein the compound is where $R_1$, $R^2$, $R^3$ and $R^4$ are methyl.

10. The method of claim 9, wherein the compound is where $R^5$ is H.

11. The method of claim 8, wherein the cancer is colon cancer.

12. The method of claim 8, wherein the cancer is melanoma.

13. The method of claim 8, wherein the cancer is breast cancer.

* * * * *